(12) United States Patent
Kaul et al.

(10) Patent No.: US 10,642,046 B2
(45) Date of Patent: May 5, 2020

(54) AUGMENTED REALITY SYSTEMS FOR TIME CRITICAL BIOMEDICAL APPLICATIONS

(71) Applicant: Cloud DX, Inc., Brooklyn, NY (US)

(72) Inventors: Robert Kaul, Brooklyn, NY (US); Sandeep S. Kohli, Oakville (CA); David Widman, Oakville (CA); Sara Ross-Howe, Campbellville (CA)

(73) Assignee: CLOUD DX, INC., Brooklyn, NY (US)

( * ) Notice: Subject to any disclaimer, the term of this patent is extended or adjusted under 35 U.S.C. 154(b) by 44 days.

(21) Appl. No.: 15/939,190

(22) Filed: Mar. 28, 2018

(65) Prior Publication Data

US 2019/0302460 A1    Oct. 3, 2019

(51) Int. Cl.
*G06F 3/038* (2013.01)
*G09G 5/00* (2006.01)
(Continued)

(52) U.S. Cl.
CPC ........ *G02B 27/0172* (2013.01); *A61B 5/6801* (2013.01); *G06T 19/006* (2013.01);
(Continued)

(58) Field of Classification Search
CPC .......... G02B 2027/0178; G02B 27/017; G02B 27/0172; G02B 2027/014; G02B 2027/0185; G02B 2027/0138; G02B 27/0179; G02B 6/34; G02B 27/0127; G02B 27/0101; G02B 2027/0105; G02B 2027/0187; G02B 27/42; G02B 27/4205; G02B 27/4227; G02B 6/10; G02B 27/0093; G02B 27/225; G02B 27/2278; G02B 6/32; G06F 16/7837; G06F 3/04815; G06F 3/011; G06F 3/017; G06F 3/0304; G06F 19/325; G06F 3/005; G06F 3/013; G06F 3/04842; G06F 3/04845; G06F 3/0485; G06F 3/0487; G06F 3/04883; G06F 3/016; G06F 3/0482; G06K 9/00664; G06K 9/00671; G06K 9/00214; G06K 9/00355; G06K 9/00389; G06K 9/00711; G06K 9/6201; G06K 9/6212; G06K 9/6215; G06T 19/006; G06T 7/60; G06T 2207/10024; G06T 2207/10148; G06T 2207/10152;
(Continued)

(56) References Cited

U.S. PATENT DOCUMENTS

2015/0242575 A1* 8/2015 Abovitz .............. G06F 16/7837
705/2

* cited by examiner

*Primary Examiner* — Insa Sadio
(74) *Attorney, Agent, or Firm* — Stephen E. Zweig

(57) ABSTRACT

An augmented reality system and method configured to automatically provide a user, such as a physician, with a real-time heads-up view of a patient's real-time medical status using an augmented reality headset. The system can automatically identify patients, pull up relevant medical records, obtain real-time biomedical sensor data from the patient, and display this to the user while, at the same time, allowing the user to directly view the patient through the headset's transparent lenses, and leaving the user's hands free to manipulate the patient or perform other functions. The system and method are particularly useful for intensive care units and other emergency medical situations where the user needs to get an almost instant understanding of the patient's status.

20 Claims, 9 Drawing Sheets

(51) Int. Cl.
    *G02B 27/01*     (2006.01)
    *G06T 19/00*     (2011.01)
    *A61B 5/00*     (2006.01)
    *G16H 10/60*     (2018.01)
    *G16H 50/20*     (2018.01)
    *G10L 15/00*     (2013.01)

(52) U.S. Cl.
    CPC ............. *G10L 15/00* (2013.01); *G16H 10/60* (2018.01); *G16H 50/20* (2018.01); *G02B 2027/014* (2013.01); *G02B 2027/0138* (2013.01); *G02B 2027/0141* (2013.01); *G02B 2027/0178* (2013.01); *G02B 2027/0196* (2013.01)

(58) Field of Classification Search
CPC ....... G06T 2207/30041; G06T 2200/04; G06T 2200/24; G06T 2207/10004; G06T 2207/30196; G06T 2210/41; G06T 2219/024; A61B 2562/0204; A61B 2562/0219; A61B 2562/0247; A61B 3/0008; A61B 3/022; A61B 3/024; A61B 3/028; A61B 3/063; A61B 3/066; A61B 3/08; A61B 3/085; A61B 3/10; A61B 3/1015; A61B 3/102; A61B 3/1035; A61B 3/113; A61B 3/12; A61B 3/1216; A61B 3/13; A61B 3/14; A61B 3/165; A61B 5/0059; A61B 5/0066; A61B 5/0077; A61B 5/01; A61B 5/0476; A61B 5/0496; A61B 5/14532; A61B 5/1455; A61B 5/14555; A61B 5/6803; A61B 2034/101; A61B 34/10; A63F 13/00; A63F 13/213; A63F 13/428; G01B 11/303; G06Q 30/0643; G16H 40/00; G16H 40/20; H04B 10/2504; H04N 13/239; H04N 13/344; H04N 13/395
See application file for complete search history.

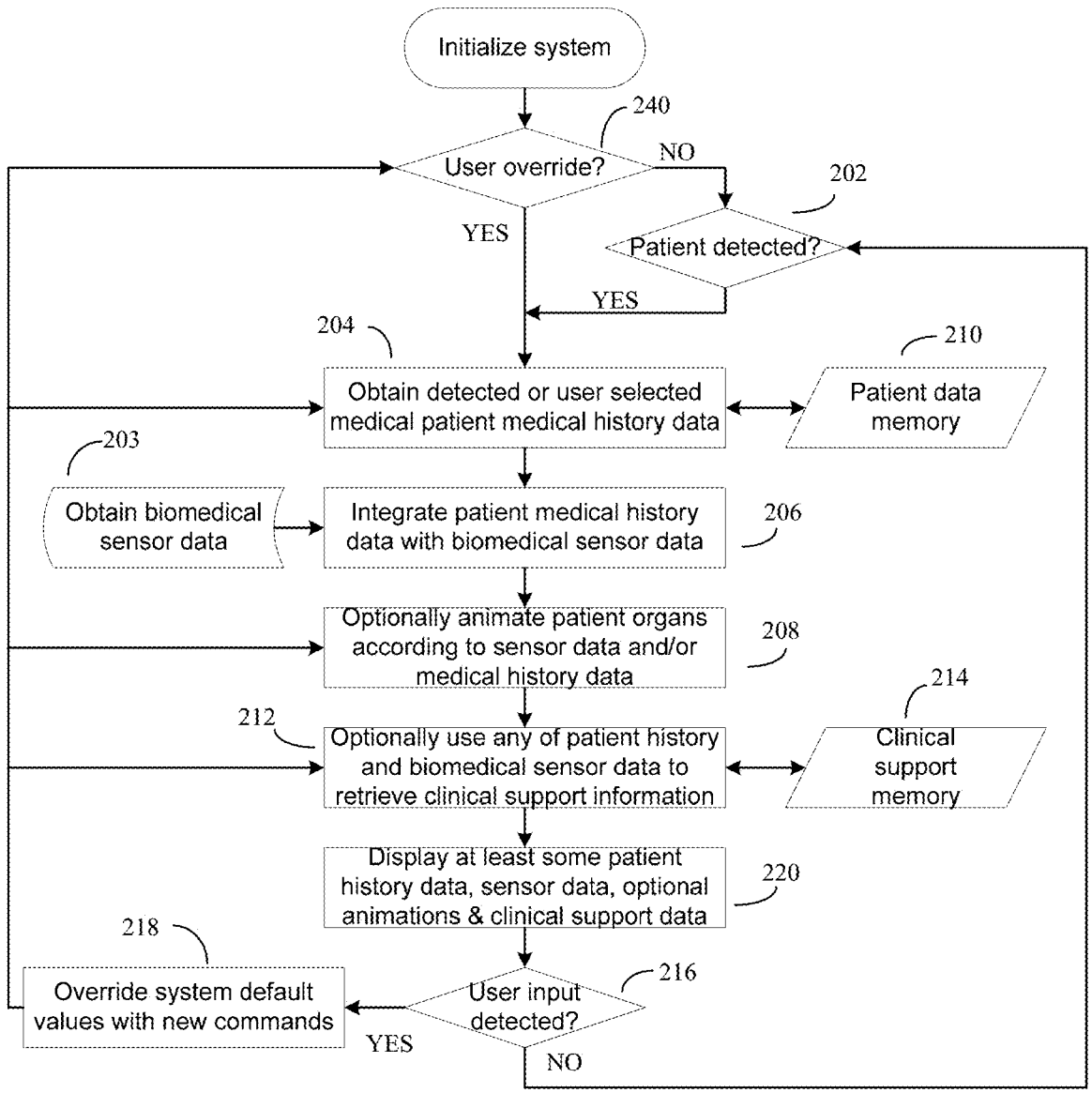

Patient 100A

Patient 100B

Patient medical data

| Patient | Right lung | Left lung |
|---|---|---|
| 100A | Normal | Normal |
| 100B | Normal | Lower lobectomy |

Real time sensor data

| Patient | Pulse | Respiration |
|---|---|---|
| 100A | 72 | 10 |
| 100B | 120 | 20 |

Resulting animation

AUGMENTED REALITY SYSTEMS FOR TIME CRITICAL BIOMEDICAL APPLICATIONS

BACKGROUND OF THE INVENTION

Field of the Invention

This invention is in the field of augmented reality devices, systems and methods related to biomedical applications.

Description of the Related Art

In recent years, various methods of using head-mounted displays and augmented reality techniques to provide medical information have been proposed. In particular, technologies such as Google Glass, Microsoft HoloLens, and other devices have been proposed for a variety of different medical functions.

The Microsoft HoloLens system, discussed in US patent publication 2017/0357333, the entire contents of which are incorporated herein by reference, teaches a head-mounted display device with a see-through (transparent or partially transparent) display, one or more computer processors, sensors such as accelerometers and tilt sensors, as well as cameras and depth cameras (e.g. time of flight cameras, often called ToF cameras) that are configured to view the outside world. This type of device often has rechargeable batteries, and wireless transceivers (e.g. Wi-Fi and Bluetooth transceivers) enabling the HoloLens to exchange information with outside computerized devices and systems.

Such augmented reality devices and methods are presently popular for various medical educational purposes, such as teaching anatomy, and other educational situations. However use of such techniques in non-educational medical environments, such as hospitals, intensive care units, and routine clinical practice has not yet become common.

BRIEF SUMMARY OF THE INVENTION

The invention was originally inspired, in part, by the insight that patient survival in certain fast-paced medical environments, such as intensive care units, is presently suboptimal. Part of the reason for this problem is that the medical staff often needs to monitor many patients simultaneously. Further, the composition of the medical staff is constantly changing, as different members rotate over each 8, 12, or 24-hour shift. At each shift change, the latest patient status information must be quickly transferred from the outgoing shift to the incoming shift. This need for rapid transfer, coupled with the limitations of human memory, greatly limits the amount of information that the medical staff has in their heads at any given time regarding the present (e.g. real-time) status of any given patient.

In an intensive care situation, these patients may, at any time, experience heart failure or other urgent condition, where a difference of a few seconds or minutes in medical response time can greatly impact patient survival.

Consider the situation from the standpoint of an attending physician, who may be responsible for many intensive care patients during that physician's shift. At any given time, one of these patients may "crash". The attending physician is expected to make a decision within a few seconds regarding the appropriate procedures or medications necessary to save the patient, but may not even have ever seen this patient before. At the same time, the attending physician needs to observe the patient, and often manipulate the patient as well.

Prior art medical records systems are poorly suited for such situations. In order to assess the patient's present state and determine appropriate action, the physician must often thumb through a folder of printed records, while simultaneously trying to look at multiple instruments that may be positioned at various places around the room, and then integrate these with the physician's own observations of the patient. While this is occurring, critical time is being lost. The invention was originally inspired by the underlying need to find systems and methods to help overcome the deficiencies of the prior art in this regard.

More specifically, the invention was inspired, in part, on the insight that patient survival in such situations can be significantly enhanced by providing an improved medical information system that allows the user complete freedom of motion (i.e. does not tether the user to a particular location with physical wires or cables), and provides a hands-free "heads-up" display that quickly provides instant access to the most relevant patient medical information. At the same time, the invention (sometimes also referred to as method or system) allows the physician to directly observe the patient, and also continue to manipulate the patient (or other medical materials) with the physician's hands.

The invention is also inspired, in part, on the insight that present head mounted display devices, such as the Microsoft HoloLens, can, with appropriate hardware and software accessories, modifications and extensions, serve as a useful Heads-up augmented reality display system for such an improved medical information system.

Although the invention was originally inspired by medical intensive care problems, the invention itself can have more general applications. In alternative embodiments, the invention can more generally be considered to be a system and method by which human users (including but not limited to physicians) can rapidly and nearly effortlessly obtain physiological information on human subjects (including, but not limited to, human subjects). For example, in some alternative embodiments, a sports coach (user) might use the invention to get near instant feedback on the physiological status of various sports team players (subjects) during a game and use this information to determine when to replace players. Thus in a more general embodiment, the term "patient" used herein may be replaced with the alternative term "subject" or "human subject". Similarly, although the invention often refers to "users" who are physicians, in principle any human can use the invention, so the term "user" is also not intended to be limiting.

BRIEF DESCRIPTION OF THE DRAWINGS

FIG. 1B shows a software flow chart according to one embodiment of the invention.

FIG. 5 shows the physician examining the patient directly, while at the same time the system is displaying various types of real-time biomedical sensor data such as heart rate, blood pressure, respiration, $SpO_2$, and the like.

DETAILED DESCRIPTION OF THE INVENTION

Figure 1A:
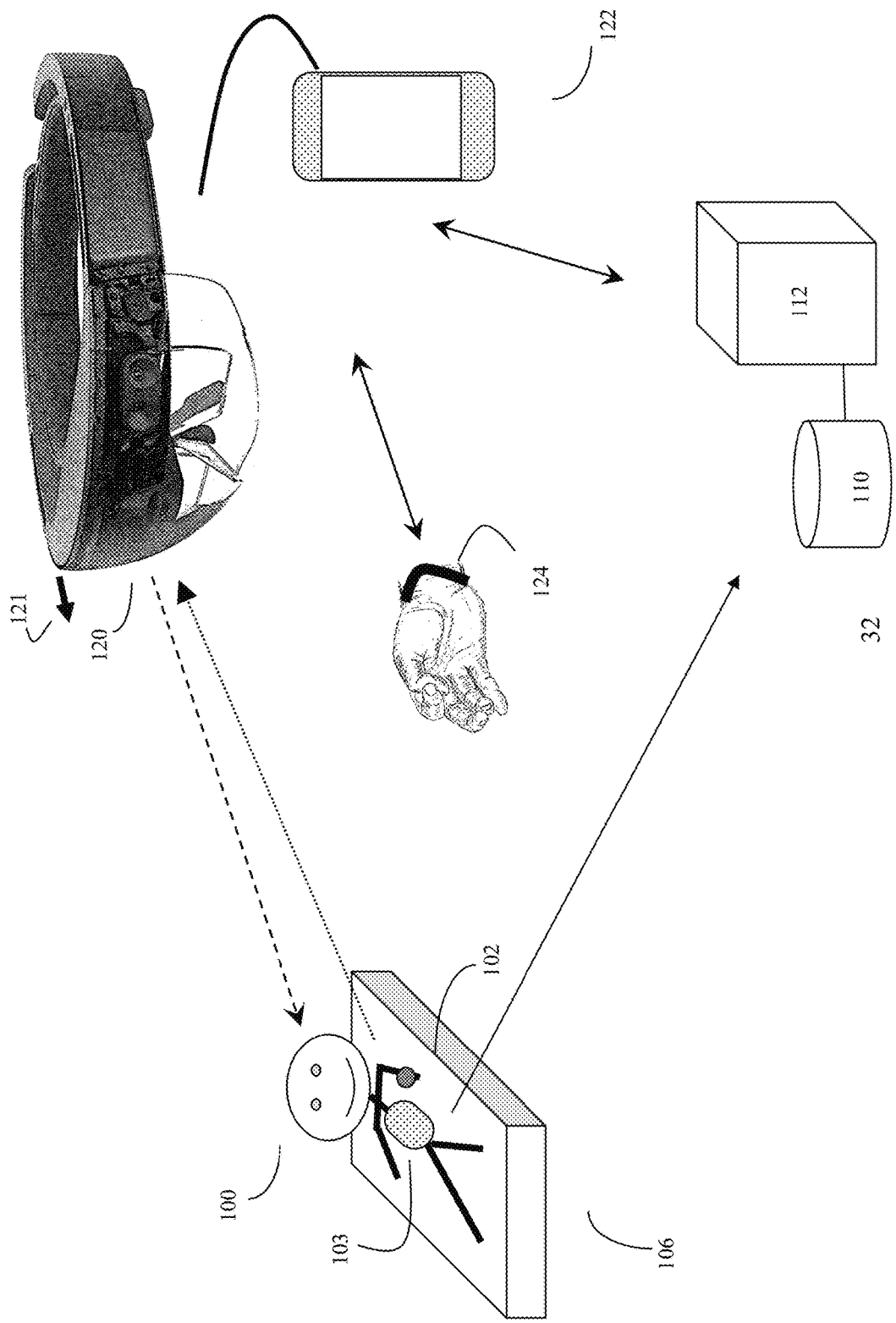
FIG. 1A shows an overview showing some of the major components of some embodiments of the invention (system).

As shown in FIG. 1A, in some embodiments, the invention may be a system, device, or method of automatically and quickly displaying patient medical information on an augmented reality headset (120) worn by a user, such as a physician. Augmented reality headset (120) may be a commercially available headset, such as the Microsoft HoloLens, exemplified by US patent publication 2017/0357333, the entire contents of which are incorporated herein by reference, or other type augmented reality headset, including custom built headsets.

When using commercially available components, the invention will typically be implemented, at least in part, by custom software, configured to perform the various functions and methods described herein. The invention's software methods need not be performed on the headset (120) alone, but in some embodiments can comprise various mutually communicating software modules that in some embodiments can run on any of headset processors (120), portable computerized device processors (122), and processors residing on local or remote servers such as (112).

Different processor types may be used. For example, the headset or portable computerized device processors may comprise one or more processor cores that may be variants of the popular ARM architecture, while the server processors may comprise one or more processor cores that may be variants of the popular x86 or x86-64 architecture, and the like. The invention's software methods may similarly be either run on (e.g. be an application), or be a part of (e.g. embedded in the operating system itself), various operating systems such as iOS, Android, Linux, Windows, or other operating system. Similarly the computer memory used for the various methods described herein need not be localized on any one device such as headset (120) alone, but also can reside on other devices such as any of headset memory (120), portable computerized device memory (122), and local or remote servers (112) and memory (110).

Note that regardless of if the augmented headset (120) operates alone or connected to a portable external computerized device (122), any combination of the headset (120) and optional portable external computerized device (122) will be self-contained so that the user can move about freely, and there are no cables, wires, or other physical connections between any of (120) or the combination of (120) and (122) and the surrounding environment.

Expressing the concept in methods format, the method may comprise using at least one computer processor (which may be incorporated into an augmented reality headset (120), or alternatively may be in a portable external computerized device (122 such as a smartphone) in wired or wireless communication with the augmented reality headset) to determine when the headset (and hence the user wearing the headset) is in proximity to a particular patient (100). In a preferred embodiment, this identification may be fully automatic, however, in an alternative embodiment, this identification may be semi-automatic and require some input from the user.

In a preferred embodiment, the invention may also automatically use at least one sensor to determine the patient's identity (or patient identity information, which may be a patient code), and often automatically request and obtain medical information history data pertaining to the patient from external memory (110). However, in alternative embodiments, this may be semi-automatic and require some input from the user.

Various types of sensors may be used to determine when the user and headset are in proximity to a patient, as well as to identify the patient. In some embodiments, the patient may be equipped with, or associated with, patient identification tags or patient-attached biomedical sensors comprising short-range wireless transceivers, such as a short-range Bluetooth™ transceiver, ZigBee transceiver, or other alternative short range wireless device (102). In other embodiments, to reduce the possibility that such short-range wireless devices may cause interference with other electrical equipment, alternative devices, such as patient associated (e.g. patient-worn) tags comprising infrared transceivers or beacons may also be used (102).

Indeed, in some embodiments, the headset (120) itself may be equipped with its own infrared data transmission system to, for example, communicate with outside computers and networks when the use of more conventional wireless systems, such as WiFi wireless methods, is considered to be unsuitable (e.g. due to radio-frequency interference with other equipment). In general, any of the wireless methods described herein may alternatively be implemented by infrared data transmission methods, such as Infrared Data Association (IrDA) methods.

Alternatively, the invention may track the location of the user and/or the headset, and use the user and/or user headset's location, in association with a patient location database (e.g. a hospital database 110) that stores or tracks the location of various patients, to identify a patient (100) on the basis of the user's present location, and the patient's location (106) as stored in the patient location database.

In other embodiments, the headset (120) may be equipped with various microphones, and the invention may use the sounds associated with the headset's present location, at least one computer processor, and suitable sound identification and triangulation algorithms to identify the position of the headset.

In other embodiments, the invention may use headset (120) mounted video cameras, depth cameras such as Time of Flight cameras, and suitable processors and computer vision algorithms, to identify the location of the user and headset, as well as in some cases to identify the patient, either by facial recognition, or by computer vision scanning of a bar code or other optically encoded patient-worn identification tag, such as a patient-worn bracelet.

Not all headset location or patent identification methods need to use headset associated devices. In some alternative embodiments, the system may use ancillary devices and sensors, such as a user-worn smartphone (122) associated sensors and processors, to identify the user's location and/or the identity of the patient.

Additionally, in a preferred embodiment, the invention will typically also use its at least one computer processor (again often headset-mounted, but which may in a different computerized device in wired or wireless communication with the headset), to further acquire real-time biomedical sensor data (such as from device 103) pertaining to this patient. In a preferred embodiment, this will be done using any of a wireless or infrared data link between the biomedical sensor and any of the headset or computerized device, so that the user when using the headset has unrestrained mobility. That is, at least the combination of the headset (120) and any optional computerized device (122) is self-contained and is not tethered to any other devices by any cables, wires, or other physical links. In a preferred embodiment, the invention will then typically automatically display at least some of this medical history data pertaining to this patient, and at least some of the real-time biomedical sensor data pertaining to the patient.

Alternatively, if no medical patient history data is available, the system can automatically inform the physician that no medical history is available. (e.g. patient name and status unknown).

The medical history data could be as little as the patient's identification or other standard data (e.g. name, age, sex, contact information), or could be as extensive as a complete medical record of the patient complete with patient medical scans, images, lab results, in the like. In some embodiments, the medical history data could also comprise various medical directives, such as advance medical directives, do not resuscitate (DNR), instructions regarding analgesia, allergies, intervenous hydration, breathing machines, cardiopulmonary resuscitation (CPR), and the like. Contact information regarding persons authorized to make medical decisions may also be provided.

Although the system may be configured to retrieve patient data while the user is remote from the patient (e.g. upon a command, such as "show me the present status of John Doe") in some embodiments, to reduce distractions in densely populated intensive care units, the system may be configured to automatically, or upon user command, only show this information when the augmented reality headset is in close proximity (e.g. within about 5, 10, 20, or 30 feet) of a given patient. This allows a physician to quickly make rounds and receive automatic patient specific updates without having to constantly adjust the system.

FIG. 1A shows an overview showing some of the major hardware components that may be present in some embodiments of the system, and FIG. 1B shows a flowchart illustrating how some of the software may operate in some embodiments of the invention. In FIG. 1A, a patent (100) is shown in a bed, here assumed to have a known location (106). In some embodiments, the patient may be wearing an optional machine-readable identification tag (e.g. bar code, RFID tag, wireless tag, infrared tag 102) and/or one or more optional patient-worn biomedical sensors (103). In some embodiments, both the identification tag (102) and the patient-worn biomedical sensors (103) may be on the same device.

The patient may also be connected to one or more other non-patient worn biomedical sensors (not shown).

At least some portions of the patient's medical record may be stored in machine-readable form as one or more electronic medical records in either local or remote memory (110). This memory can be local (intranet) memory (e.g. various local devices or local servers) or remote (internet) "cloud" servers (112). The data in this patient medical record is shown in FIG. 1B as (210).

In some embodiments, the augmented reality headset worn by the user may be a Hololens or similar type device, which may be a commercially obtained (e.g. off the shelf) type augmented reality headset (120). Alternatively, the headset may a custom headset. The augmented reality headset will typically comprise any of eyeglasses and goggles, with transparent lenses mounted over each eye allowing the user to directly see the outside world (e.g. directly see the patient 100 through the transparent lens). Here we will refer to this direct viewing of the outside world as receiving images of the outside world.

The headset will typically also have at least one computer display configured to overlay the direct images of the outside world with additional computer-generated bit-mapped graphics, preferably in a semi-transparent manner so that the computer images do not completely obscure the direct images of the outside world. However, if desired, the overlay may be non-transparent.

The augmented reality headset may, in some embodiments, also comprise at least one patient location sensor, at least one augmented reality headset computer processor configured to drive the bit-mapped graphics, and at least one communications interface (such as a wireless transceiver or wired computer interface) configured to at least obtain medical history data from an outside source, such as memory (110) from server (112). Alternatively or additionally, the headset may receive additional computer processor services, memory, and even power from the additional user-worn devices, such as a smartphone or tablet type device (122). The flowchart shown in FIG. 1B is primarily focused on showing some of the software operations that can be performed by these various computer processors.

More specifically, in some embodiments, the medical history data may be obtained from any of augmented reality headset memory (e.g. memory that is part of headset (120)), local intranet electronic medical (110) record memory, or memory stored on at least one remote internet server (also shown as 110). Memory in other local computerized devices such as a smartphone (122) may also be used to store and retrieve at least some medical history data. Any of these should be considered to hold the patient data memory (210) shown in FIG. 1B.

As previously discussed, in some embodiments, the augmented reality headset (120) may be equipped with one or more patient proximity sensors. These can be wireless proximity sensors configured to detect an optional identification tag or patient associated biomedical sensors (102, 103). The patient proximity sensors can also be headset mounted video camera and associated automated vision systems equipped with facial recognition systems. Other methods, such as headset position sensors configured to automatically pull up patient information associated with certain beds (106) or rooms can also be used when the user is in the proximity to these locations. Data from these sensors can be used to enable the system software to determine if a patient has been automatically detected by the system in FIG. 1B step (202).

The system can alternatively be voice activated for these purposes. This is an example of one type of user override that is shown in more detail in FIG. 1B step (240). In some embodiments, the system may be configured to operate automatically if there are no overriding user commands (user overrides), but then to override this automatic operation and replace the automatic operation with specific user commands when the user so decides.

As a semi-automated approach, which is an example of one type of user override, the system may also be configured to accept voice input from the user by using microphones and suitable speech recognition software running on a headset associated computer processor(s).

The augmented reality headset (120) may, in some embodiments, also be connected (either by a wired or wireless link) to a user-worn computerized device (122), which may be a smartphone or other portable computerized device equipped with software to implement at least some of the invention's methods, and which may contain some or all of the processors needed to implement the invention. For example, in FIG. 1B, it may be convenient to perform some of the operations using a computer processor that is part of the headset (120) itself, but to offload some of the other operations to external processors (e.g. processors in 112, 122) as well.

The augmented reality headset (120) or user-worn computerized device (122) may also be connected (either by a wired or wireless link) to additional haptic sensors, touch sensors (e.g. touchpads, touchscreens) or motion sensors or transducers or other user interface devices, such as hand worn haptic sensors or motion sensors (124) or other user interface devices to enable the system to be controlled by various user gestures, as desired. This enables the user to, for example, control (or generate user overrides) the system by certain gestures while, at the same time, leaving the hands free. Here device (124) may comprise suitable motion sensors and a short-range wireless transceiver in communication with either headset (120) or other user-worn computerized device (122).

Thus in a preferred embodiment, the system may be configured to work in an automatic or nearly automatic hands-free configuration so as to free the user's hands for other purposes. However various means of user input may still be used. For example, the system (e.g. the augmented reality handset (120) or smartphone (122) and at least one computer processor can be configured to receive input from the user by any of voice (e.g. headset 120 or smartphone 122 may have a microphone and optional voice recognition capability), hand motion sensors (124), and haptic or touch (e.g. touchpad or touchscreen) sensors (124).

Expanding on the voice control option, in some embodiments, it may be useful to equip the headset with one or more microphones, and use speech recognition software (and processors located either in the headset 120 or smartphone 122) to obtain vocal commands from the user, such as: "show patient 2304" or "show John Doe". In these embodiments, these vocal commands may alternatively be used to inform the system when the user is in proximity to the patient, the identity of the patient, and also as a command to obtain that patient's medical history data from memory (110) and/or real-time sensor data from sensors (102).

The system can also be configured to easily transition from an automatic mode to a semi-automatic or manual mode. For example, outside of an intensive care unit, the user may prefer to revert to a semi-automatic mode and have greater control over what patient data is shown, and when. At the same time, in an intensive care unit, ambulance, or battle (military) situation, the user may find it preferable to put the system into the fully automatic mode, thus freeing the user to concentrate on other issues. If, for example, 50 patients come in the door at the same time from a mass accident, automatic mode may be preferrable.

An important distinction between the present art and prior art is that the system also can be configured to automatically show real-time biomedical sensing data from the patient. In some embodiments, this sensor data can be obtained from standard hospital or clinic sensors, often by way of wireless communication between the headset (120) or smartphone (122) and the local medical information system that manages the various sensors. Alternatively, the various sensors (103) can also communicate directly with the headset (120) or smartphone (122), often using wireless transceivers.

In some embodiments, which may be particularly useful in emergency medical situations, such as ambulances, military medicine, and the like, at least some of the real-time patient data can be obtained using unitized patient-worn biomedical sensing systems (103). This biomedical sensor data is shown as (203) in FIG. 1B. An example of a more sophisticated type of unitized patent worn biomedical sensing system is shown in FIG. 2.

Figure 2:
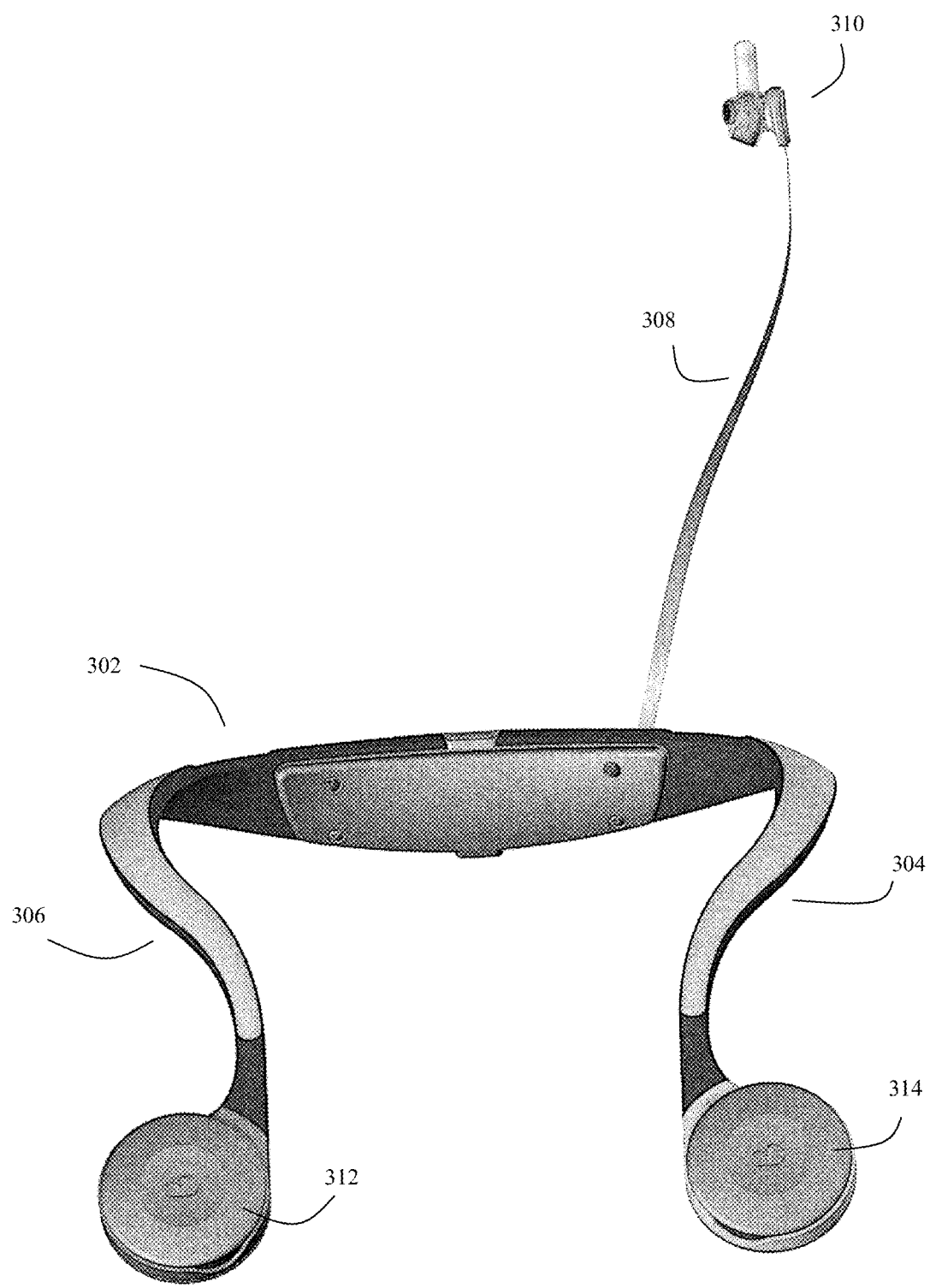
FIG. 2 shows an example of a unitized patient-worn biomedical sensing system that may be used to obtain real-time patient biomedical data according to some embodiments of the invention.

FIG. 2 shows an example of a unitized patient-worn biomedical sensing system that may be used to obtain real-time patient biomedical data according to some embodiments of the invention. This corresponds to FIG. 1A from commonly owned and invented US patent application 2017/000359, incorporated herein by reference.

In this embodiment, patient (100) may be equipped with a unitized (e.g. potentially ambulatory patient wearable) vital sign monitoring sensors (103), which may comprise one or more sensors such as ambulatory patient wearable ECG sensors, pulse oximeters, electronic stethoscope(s), and oscillometric blood pressure monitors. These sensors are configured to transmit sensor data (203) to a wearable computerized device such as the present invention's augmented reality headset (120), or to local or remote memory (110), or other computerized devices. See US patent publication 2017/000359, incorporated herein by reference, for further discussion.

For example, in some embodiments, the unitized patient wearable sensors (103) may comprise an open front collar (302) with various physiological and environmental sensors. These may comprise one or more onboard vital sign sensors, such as: ECG, $SPO_2$ (PPG), Thermopile sensors, as well as various environmental sensors such as accelerometers, gyroscopes, and GPS sensors.

The front of this device may have two adjustable arms (304, 306) which extend down towards the user's chest. At the bottom of these arms, on the side which faces the user's skin, a snap type fitting may be positioned to accept ECG electrodes, such as wet (sticky) ECG electrodes (314, 312). Dry contact leads may also be used in some embodiments. In this embodiment ECG data may be captured below the patient's clavicle, using two leads symmetric about the sternum which approximate the V1 (4th intercostal space, right of the user's sternum) and V2 (4th intercostal space, left of the user's sternum) leads of traditional ECG equipment. In some embodiments, additional leads may be attached to such described device as desired.

This neck mounted device may be worn around the user's neck and shoulders, and in some embodiments may also have an appendage (e.g. cable 308) going up the patient's ear(s) with an optional ear attachment device (310).

Thus in this embodiment, the neck mounted patient-worn biomedical sensors may contain at least an ECG sensor, batteries, an optional computer processor, memory, and circuitry to drive both the ECG sensors and other sensors. The optional earpiece will often also have PPG and Thermopile sensors, which may, for example, be driven by the electrical circuitry and power supplied by the neck mounted device through a cable (308), or by other methods such as internal earpiece batteries. The electrical circuitry may also have wireless sensors or infrared sensors to transmit the biomedical sensor data (203) either directly to the headset (120), or indirectly to the headset via other devices such as clinic computer system (112, 110), or other computerized device, such as user-worn smartphone (122).

Thus in some embodiments, at least some of the real-time biomedical sensor data (FIG. 1B 203) may be obtained from one or more unitized patient wearable vital sign monitoring sensors (103).

Here "unitized" means that the vital sign monitoring sensors can be configured to be capable of being worn by an ambulatory patient, even though the patient might not actually be ambulatory. An alternative term to "ambulatory" in this case may be "self-contained" or patient wearable without mechanical connection to external devices. Alternatively, of course, standard biomedical sensors not configured for use by ambulatory patients, and which may be connected to relatively stationary monitors, may also be used.

Thus the unitized patient wearable sensors may comprise one or more ambulatory patient wearable sensors, such as any of an ECG sensor, pulse oximeter, and pulse monitor or oscillometric blood pressure monitor. As previously discussed, these various wearable sensors can be configured to transmit sensor data either directly to the headset (120) or smartphone (122), or indirectly to the augmented reality headset via a local medical computer system such as (112).

Alternatively, as previously discussed, conventional (e.g. not patient-worn) sensors linked to various room monitoring equipment may also be used, as long as the room equipment is configured to transmit this data in real time to the invention.

Use examples:

In these examples, assume that the physician has previously triggered the system to work in a fully automatic mode so that the system is automatically bringing up information according to the invention.

Figure 3:
FIG. 3 shows a physician, equipped with the system's headset (lower left), about to enter a patient's room.

FIG. 3 shows a physician (user), equipped with the system's headset (120 lower left), about to enter a patient's room. The main portion of the figure shows the augmented reality scene from the perspective of the physician (user). Note that the physician is not yet close enough to the patient for the invention to automatically populate the augmented reality display with patient data. This corresponds to the situation in FIG. 1B where there is no user override (240), and the patient has not yet been detected in (202).

Figure 4:
FIG. 4 shows the same scene a fraction of a second later. The physician is now close enough to the patient for the invention's patient proximity detectors to register proximity to the patient, and the system has now started to automatically populate the augmented reality display with at least some patient data.

FIG. 4 shows the same scene a fraction of a second later. The physician is now close enough to the patient for the invention's patient proximity detectors to automatically register proximity to the patient, and the system has now started to automatically populate the augmented reality display with at least some patient data. Note that in some cases, such as a mass accident situation, no patient data may be available. In this case, the absence of patient data is itself a type of patient data (e.g., patient data=null), so the system can report the absence of patient data by appropriate output such as "patient data—".

This corresponds to FIG. 1B (202) where the patient has now been detected, and the system software is progressed through steps (204) to obtain the patient data from memory (210) and has also obtained the biomedical sensor data (203), integrated this with the patient medical history data (206), is animating the patient's organs according to the biomedical sensor data (208), and is now displaying the data on the augmented reality headset (220), (120). However, no clinical support information (212) is being shown.

As previously discussed, in this embodiment, the physician (user) has decided that it would be useful to configure the system so that the headset (120) is automatically populated with patient data whenever the user is near the patient, even without any additional user input. However what happens if there are many patients in close proximity?

In some situations, (such as a crowded intensive care unit), this may be distracting, and the user may only want to see patient data when the user is looking in the general direction of a particular patent.

To enable the ability to only show patient information when the user is looking at the patient, in some embodiments, the augmented reality headset (120) may be configured with sensors enabling the headset to detect a viewing direction (e.g. direction or orientation sensors). These direction or orientation sensors can comprise geomagnetic field sensors, gravity field sensors, motion sensors, accelerometers, gyroscope (e.g. three-axis gyroscope) based sensors, and the like. The software FIG. 1B may also be configured with suitable overrides so that just proximity to the patient is not enough to trigger the display of that patient's data.

The patent (100) will often have a defined position (106) relative to the orientation of the headset (120). For example, in FIG. 1A, the patient (100) is shown in front of the headset as indicated by arrow (121). Even when the patient (100) is close to the headset, however, the user will not always be looking at the patient (100), and as a result, the front of the headset (121) will not always be pointed in the direction of the patient.

In some embodiments, the system may use its one or more computer processors and the direction or orientation sensors (e.g. patient location sensors) to further control what is displayed on the augmented reality headset (120). For example, the system can be configured so as to suppress display of at least some or all of the patient's medical history data and/or real-time biomedical sensor data when the viewing direction of the augmented reality headset (120) is not oriented (121) towards the position of the patient (100).

Consider the situation where two patients are in close proximity. In this alternative type of automatic mode, when the physician (user) looks at patient "A", the system will use the relative orientation of the headset (121) and the patient (100) to automatically bring up data for patient "A". When the physician looks at patient "B", the system will automatically use the orientation of the headset (121) and patient B to automatically bring up data for patient "B".

Figure 5:

FIG. 5 shows the physician examining the patient directly, while at the same time the system is displaying various types of real-time biomedical sensor data (203), such as heart rate, blood pressure, respiration, SpO$_2$, and the like. The system is also animating a computer representation of certain patient organs, such as the heart and lungs, to allow the physician to better visualize some of the biomedical sensor data, optionally in the context of other patient scan data. The software module that does this is animation is shown in FIG. 1B (208).

Figure 6:
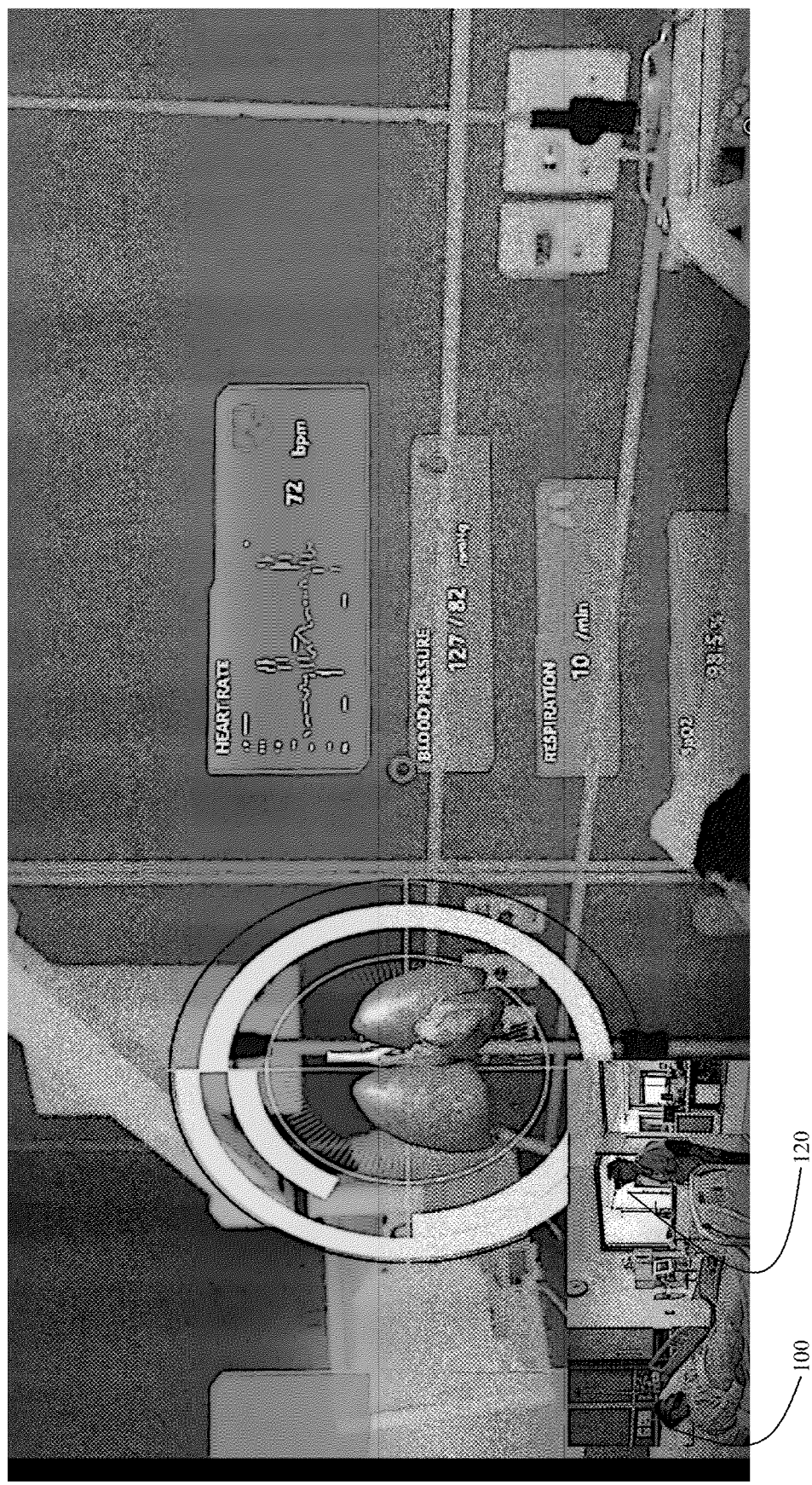
FIG. 6 shows a closer view of some of the augmented reality data.

FIG. 6 shows a closer view of some of the augmented reality data. Here the system is showing the patient's real-time heart rate, blood pressure, respiration, and SpO$_2$, and the system is also animating a representation of the patient's heart and lungs accordingly. At the same time, the physician is still free to directly observe the patient through the transparent sections of the augmented reality headset, and manipulate other objects as desired.

Some embodiments of the invention are based on the further insight that, particularly in emergency high-stress situations, it is often easier to appreciate a visual effect than it is to quickly grasp numbers. Consider, for example, pulse rates and breathing rates. When swamped with a lot of information, the numbers might not be properly noticed or appreciated. However, an animation of the heart beating unusually fast or slow, or lung respiration being visually unusual, can often be more quickly understood in such situations.

Figure 7:
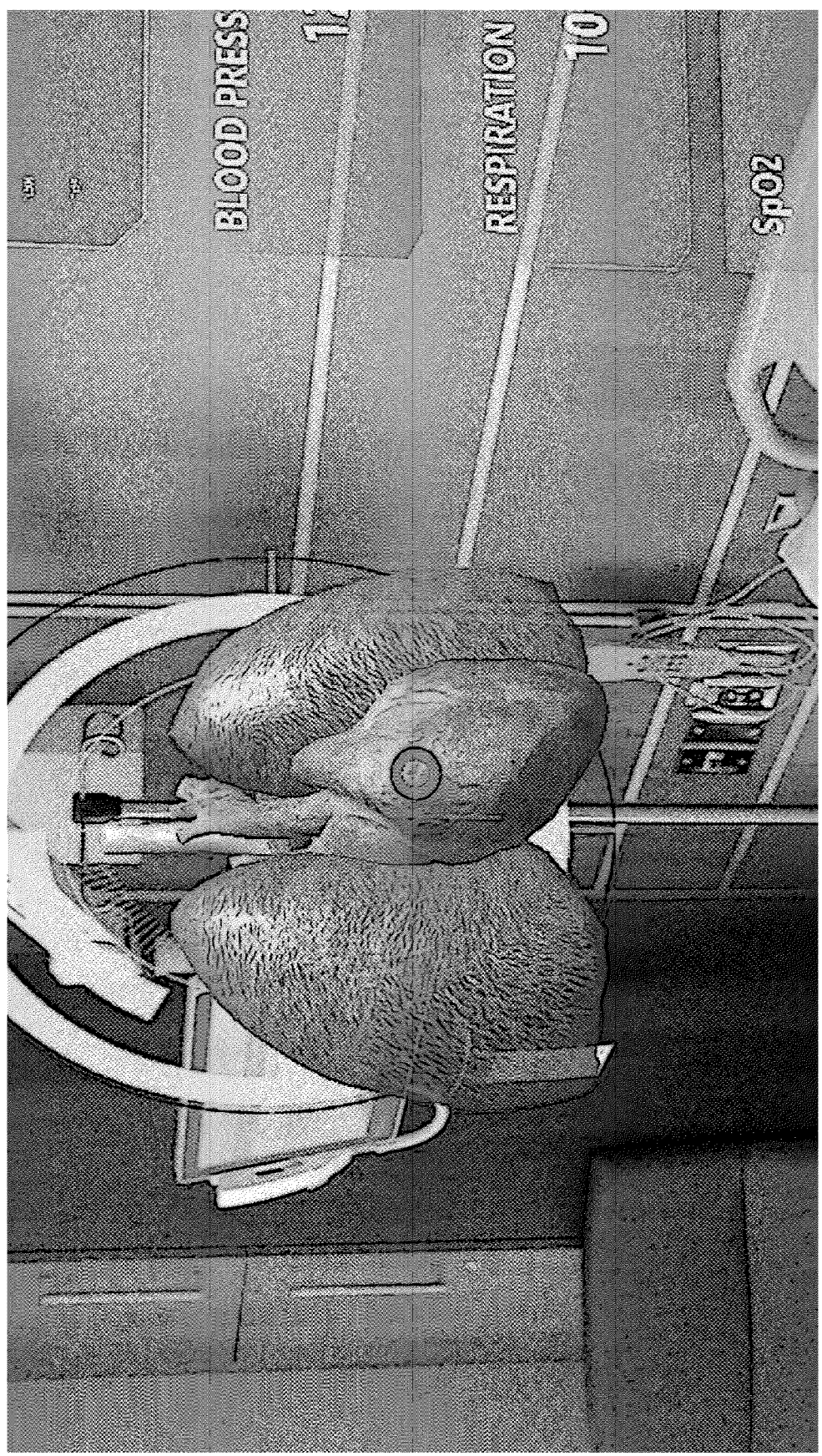
FIG. 7 shows a closer view of the computer animation of some of the patient's organs, such as the heart and lungs.

FIG. 7 shows a closer view of the computer animation of some of the patient's organs, such as the heart and lungs. Here the system is shown animating a computer model of the heart to beat according to the pulse rate, and the lung expansion and contraction according to the respiration rate. Note that the fidelity of the animation can be further enhanced by integrating other patient medical data and records. For example, if the patient has only one lung or a collapsed lung, the computer animation can be updated accordingly. If various images of the organs are available, the system can also optimally apply these images as a texture or other alteration to the underlying computer model so as to quickly convey other relevant medical information as well.

Consider an emergency situation where a patient has only one lung, and the physician has never seen the patient before. Sensor data that might be discounted under the assumption that the patient has two normal lungs can take on more urgency if the user (physician) can immediately see that the patient has only one lung, and the heart animation is beating unusually under that situation.

Thus, for example, in some embodiments, the biomedical sensor data (103, 203) may comprise cardiovascular sensor data. The system can be configured to further display the cardiovascular sensor data by using at least one computer processor (in any of headset 120 or user-worn computerized device 122, for example) to animate a computer representation of the patient's heart and lungs (FIG. 1B 208) to correspond with the cardiovascular sensor data, thereby producing a sensor responsive animation. The system can then display this sensor responsive animation on the augmented reality headset (120) (as per FIG. 7).

As previously discussed, still more realistic techniques may be used, as desired. For example, in some embodiments, the system may use its at least one computer processor to modify the computer representation according to the patient's medical history data. This would produce a medical history corrected computer representation. The system can then display this as a sensor responsive medical history with corrected animation on the augmented reality headset (120).

So, for example, returning to the one lung example, if the medical history shows that the patient has only one lung, only one lung may be shown in the animation. Known, diseased coronary arteries, tumors, and other gross pathologies can also be illustrated accordingly, giving the user an almost instant insight into the medical status of the patient because the user is seeing a visual representation of these problems.

Figure 8:
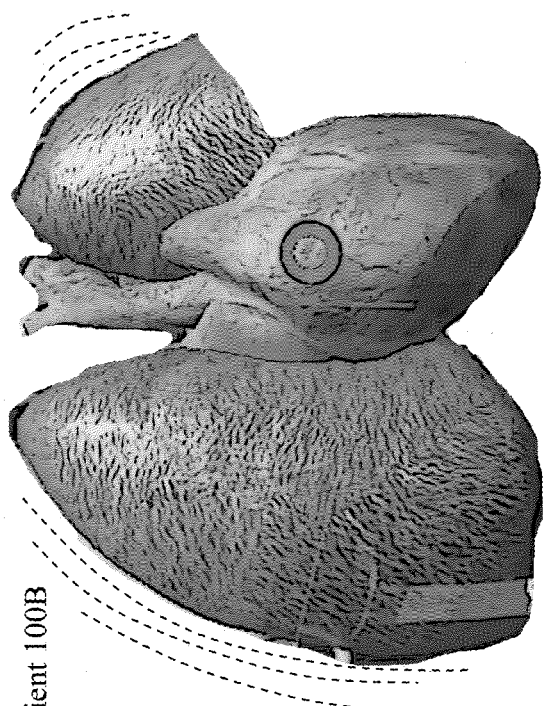
FIG. 8 shows an example of how the system can integrate patient data with real-time sensor data to produce a more realistic computer animation of some of the patient's organs.
Figure 8:
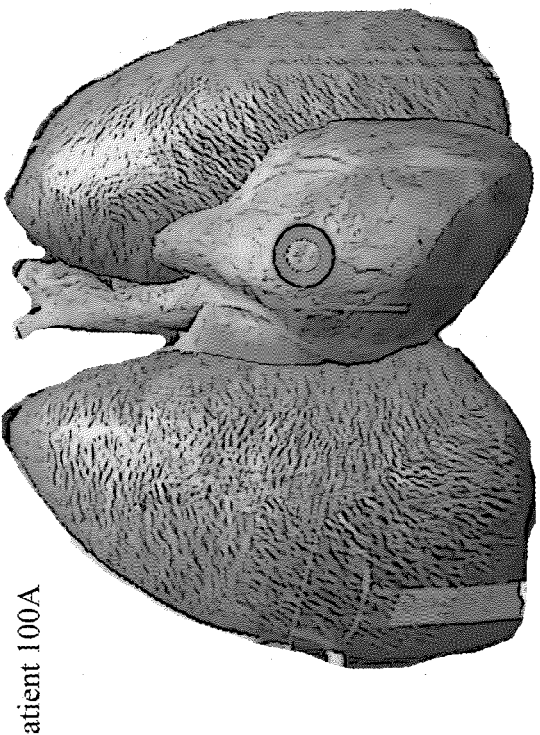
Figure 8:

An example of this embodiment is shown in FIG. 8. In this embodiment, assume that the patient medical data for patient 100A shows normal left and right lung anatomy, while the patient data for patient 100B shows that patient 100B has had a lower lung lobectomy on the patient's left lung. The system software can be configured to use the patient data to modify the underlying 3D computer representation of the patient's heart and lungs, and then further animate the data according to the real-time sensor data. In this hypothetical example, while patient 100A has a normal pulse and respiration, patient 100B has an elevated pulse and an abnormally fast respiration. The system combines the two different sets of data and shows the abnormal image on the augmented reality headset, allowing the physician user to immediately see that something is wrong.

In still other embodiments, when the medical history data may include either medical images of the patient, the system's at least one computer processor can be further configured to use the augmented reality headset (120), and at least one patient location sensor to automatically scale and transform these medical images so as to create an overlay, such as a semi-transparent overlay of least some of the medical images either over a corresponding portion of the patient's anatomy, or alternatively floating in space away from the patient, as desired. This in effect can give the user a form of "X-ray vision" (or sonogram vision, or MRI vision, etc).

Automated Clinical Decision Tools

In some embodiments, in addition to showing patient history and real-time patient sensor data, the system can also be configured to either automatically, or upon user voice command, bring up various types of clinical decision software and reference materials. This option is shown in FIG. 1B (212) and (214).

In these embodiments, the system can use its at least one computer processor, and other factors such as the patient's identity, patient's medical history (210), and/or real-time biomedical sensor data (203) to retrieve (212) from computer memory (here shown in FIG. 1B as memory 214, although memory 210 may alternatively be used) and display various types of clinical support. This clinical support can include situation appropriate clinical decision algorithms, situation-appropriate alternative potential diagnoses, and situation appropriate alternative medical treatments.

Examples of such clinical decision algorithms, alternative potential diagnoses, alternative medical treatments and the like are discussed in more detail below.

Additional Discussion

In some embodiments, the invention may be used as a comprehensive patient care management system. In these embodiments, within the system are augmented reality elements that facilitate the following functions:

1. Direct patient care (discussed below)
2. Patient education—through shared visualization of information & sharing of information.
3. Patient time management—creating and manipulating a schedule for medication administration times, monitoring schedules, exercise times, stretching times, etc. on a virtual calendar, etc.
4. Practice management—booking patient's appointments, tests, and other applications.
5. Patient referrals to other doctors and healthcare practitioners. The system could optionally also be configured to send a copy of the data displayed on the augmented reality headset to medical records, or other individuals such as to another physician to get instant advice.
6. Telemedicine or remote medicine. Here the system can also be configured to allow others to visualize what is being observed through the lens or glass remotely. In this embodiment, the system can combine a visual display from a forward mounted video camera on the augmented reality headset, with the data displayed on the augmented reality headset, and again this can be forwarded to other systems and users as desired.

Particular functions in each category:

Direct Patient Care:

In some embodiments, the system can be configured to provide a basic interface of all relevant patient information collected and displayed in one place to improve efficiency. This interface can assist with patient care by allowing the clinician to visualize the body in unique ways, e.g. by zooming into various areas, by capturing images, and by allowing the clinician to compare images over different times to assess for changes over time.

For example, as previously discussed, in some embodiments the system can be used to provide additional clinical support services (FIG. 1B, 212 and 214). In particular, the system can be very useful in helping the physician judge subtle visual changes in the patient's appearance that can be indicative of medical status.

Consider variations in the size of the patient's pupils, which can often give important information regarding the patient's neurological status. The system can provide several types of clinical support information and services here.

Here the system can use headset mounted video cameras, optionally equipped with distance measuring sensors, to help determine the size of the patient's pupil, and flag if the patient's pupils are unusually small or large.

Alternatively, the system can merely display a reference chart showing a range of pupil sizes, allowing the physician to see the patient's eyes and the reference chart simultaneously.

As a third option, the system can display an iris and pupil chart that can be adjusted by the physician by various commands, such as voice command, haptic input, and the like. For example, the physician can look at the patient's eyes, simultaneously look at a computer generated representation of the iris and pupal in the augmented reality display, and issue various commands such as "iris increase, pupil decrease" to make the chart match the appearance of the patient's pupil. This enables the physician to rapidly produce a semi-automated but computer enhanced assessment of the patient's pupils.

These basic methods can be used to assist in the evaluation of many other visible patient parameters as well. In general, the system may be used to facilitate visual assessments patient by the above method. In particular, semi-automated methods, where the system simultaneously shows a user adjustable chart, allows the user to adjust the chart to where it matches the patient, and then automatically assesses these results are particularly useful. This type of hybrid approach can combine the excellent properties of the human eye along with a semi-automated computer assessment to help provide more accurate results than a physician might obtain without the use of such a system. Other applications of such methods can include:

Assessing pupil symmetry between eyes to make diagnoses.

Looking at a rash—cross reference it to a database to make a diagnosis or look at it at previous time points to assess for improvement or/worsening Looking at a lump—cross-reference to a database to identify the cause, or ask the computer processor to list the causes of lumps, swellings in that region of the body. This can again be via simple commands such as: "Show me the list of causes of neck lumps."

Examining the face and identifying asymmetry to make a diagnosis e.g. stroke

Visualizing changes in physical characteristics over time to assist with care. For example, using the system to look at an area of the body and then using the augmented reality headset to simultaneously show a stored image from a previous time to assess for changes. Examples here can include leg swelling to see if a leg is improving or worsening, as well as the previously discussed rash, lump, pupil measurements, and the like.

Medication management systems: In some embodiments, invention's clinical support information system (FIG. 1B, 212, 214) can be used to perform various functions such as:

Pulling up a list of medications

Comparing this list to the patient medication list at previous time points

Displaying the patient's known allergies, cross-referencing the list against their current list of medications Looking and identifying interactions between drugs using a cloud-based database Assessing medication doses, e.g. calculating the correct dose based on patient weight, age or kidney function, liver function, etc.

Asking the computer processor(s) questions such as "what drug should I use to treat condition X?" Here the system can be configured to display a list of suggestions.

The system can also be used to compare patent medication administration against changes in patient vital signs or physical characteristics to assess for relationships. An example of a query here might be: "What happened to the patient's heart rate after the patient took a scheduled medication at 2 PM?"

Assessing for trends by the intelligent display of information—graphing trends of vital sign changes, blood work changes, etc. over time The system can also be used to interacting with cloud-based medical database systems to generate diagnoses, and/or assess for improvement.

In some embodiments, the invention may also be used to access patient location information (e.g. obtained from patient associated GPS sensors or other location sensors) and assess where patients have traveled or have been recently. This can then be cross-referenced with databases which contain information on areas of disease emergence, epidemics, exposure to toxins, exposure to other sick individuals, and the like.

2. Patient education—through shared visualization of information & sharing of information. In some embodiments, it is useful to configure the system's output so that the physician can share augmented reality headset information that the physician is seeing with other users. Here various techniques could be used to facilitate this process.

Further comments regarding alternative user input methods.

As previously discussed, the system user interface can be controlled by various means. In some embodiments, headset mounted video cameras, and suitable computer vision software and system processors may be used to interpret various user commands including:

Haptic or touchpad gestures (see FIG. 1A 124)

Pointing at various virtual buttons that are displayed by the headset's augmented reality display system.

In some embodiments, the headset (120) may be further equipped with at least one video camera configured to capture at least a portion of the user's face. In these embodiments, when the system's computer processor is equipped with suitable computer vision software, the system may alternatively accept user facial gesture input such as blinking, winking one eye, facial gestures, and the like.

In this way, the system's virtual interface becomes like a living record, facilitating patient care and practice management in a comprehensive way. The two functions become seamless so the doctor needs but one work canvass to do his or her job. The system can be used in inpatient/acute environments like a hospital or ER, but it could also be used in a clinic by a family doctor, or by non-doctor practitioners, dentists, chiropractors, physiotherapists, nurses, and other healthcare professionals.

Although augmented reality headsets are used as a specific embodiment of the invention, this need not be limiting. In some embodiments, the headset can be an "interactive surface display" which can broadly include HoloLens, Google glass, HUD windshield display in connected cars, reflective glass or mirror for digital info kiosks, and other types of displays In some embodiments, the invention may also cover the display, manipulation, and usage of continuous metrics (data) in the invention's augmented reality platform/environment. In addition to cardiovascular data, the system can be used to monitor many other patient physiological and physical parameters, such as heart rates (pulse rate), blood pressure, breathing rate, patient positional information (e.g. patient GPS coordinates, number of steps taken), patient oxygen levels ($O_2$ saturation), patient temperature, and patient weight.

The invention claimed is:

1. A method of automatically displaying patient medical information on an augmented reality headset worn by a user, said method comprising:
   using at least one computer processor in communication with said augmented reality headset, and at least one sensor, said at least one sensor comprising at least a patient proximity sensor, to automatically determine
   a) when said user is in proximity of said patient;
   b) determine an identity of said patient, and
   c) obtain medical history data pertaining to said patient;
   using said at least one computer processor to further acquire, from at least one patient wearable biomedical sensor currently worn by said patient, real-time biomedical sensor data pertaining to said patient;
   displaying at least some of said medical history data pertaining to said patient, and at least some of said real-time biomedical sensor data pertaining to said patient when said augmented reality headset is in proximity of said patient.

2. The method of claim 1, wherein said augmented reality headset has a viewing direction and said patient has a position, further using said at least one computer processor and at least one patient location sensor to further control said augmented reality headset so as to suppress display of at least some of said medical history data and real-time biomedical sensor data when said viewing direction of said augmented reality headset is not oriented towards said position of said patient.

3. The method of claim 1, wherein said medical history data comprises medical images of said patient; and
   at least one computer processor is further configured to use said augmented reality headset, and at least one patient location sensor to automatically scale and transform said medical images so as to create an overlay of at least some of said medical images over any of a corresponding portion of said patient's anatomy and nearby said patient, for said user.

4. The method of claim 1, wherein said real-time biomedical sensor data comprises cardiovascular sensor data;
   Further displaying said cardiovascular sensor data by using said at least one computer processor to animate a computer representation of said patient's heart and lungs to correspond with said cardiovascular sensor data, thereby producing a sensor responsive animation, and displaying said sensor responsive animation on said augmented reality headset.

5. The method of claim 4, further using said at least one computer processor to modify said computer representation according to said medical history data, thus producing a medical history corrected computer representation, and displaying a sensor responsive medical history corrected animation on said augmented reality headset.

6. The method of claim 1, further using said at least one computer processor and any of said identity of said patient, said medical history data pertaining to said patient, and said real-time biomedical sensor data pertaining to said patient to retrieve from computer memory and display any of:
   a) clinical decision algorithms;
   b) alternative potential diagnoses;
   c) alternative medical treatments.

7. The method of claim 1, wherein any of said augmented reality headset and said at least one computer processor in communication with said augmented reality headset are further configured to receive input from said user by any of voice sensors, hand motion sensors, facial gesture sensors, and haptic sensors.

8. The method of claim 1, wherein said medical history data is obtained from any of augmented reality headset memory, local intranet electronic medical record memory, or memory stored on at least one remote internet server.

9. The method of claim 1, wherein said augmented reality headset worn by a user comprises any of eyeglasses and goggles, with transparent lenses mounted over each eye allowing said user to see images of an outside world, at least one computer display configured to overlay said images of an outside world with computer generated bit-mapped graphics, at least one patient location sensor, at least one augmented reality headset computer processor configured to drive said bit-mapped graphics, and at least one communications interface configured to at least obtain medical history data from an outside source.

10. The method of claim 1, wherein at least some of said real-time biomedical sensor data is obtained from a unitized patient wearable vital sign monitoring system configured to be capable of being worn by an ambulatory patient, said monitoring system comprising:
    at least one ambulatory patient wearable sensor, said at least one ambulatory patient wearable sensor comprising any of one or more ECG sensors, pulse oximeters, temperature sensors, motion sensors, electronic stethoscope, and blood pressure monitors;
    said at least one ambulatory patient wearable sensor further configured to transmit sensor data either directly or indirectly to said augmented reality headset.

11. The method of claim 1, wherein determining any of
    a) when said user is in proximity of said patient;
    b) determine an identity of said patient, and
    c) obtain medical history data pertaining to said patient;
    is done using speech recognition input from said user.

12. The method of claim 1, wherein said at least one sensor comprises any of a short-range wireless transceiver, RFID tag sensor, headset mounted video camera, user location sensor, microphone, or infrared sensor.

13. A system configured to automatically display patient medical information on an augmented reality headset configured to be worn by a user, said system comprising:
    an augmented reality headset configured to be worn by said user;
    at least one sensor, said at least one sensor comprising at least a patient proximity sensor;
    at least one computer processor in communication with said augmented reality headset and sensor, said at least one computer processor configured to use data from said at least one sensor to automatically determine:
a) when any of said headset and said user is in proximity of said patient;
b) determine an identity of said patient, and
c) obtain medical history data pertaining to said patient;
said at least one computer processor further configured to acquire from at least one patient wearable biomedical sensor currently worn by said patient, real-time biomedical sensor data pertaining to said patient;
said at least one computer processor and said augmented reality headset further configured to display, at least while said augmented reality headset is in proximity to said patient, at least some of said medical history data pertaining to said patient, and at least some of said real-time biomedical sensor data pertaining to said patient.

14. The system of claim 13, wherein said medical history data comprises medical images of said patient; and
at least one computer processor is further configured to use said augmented reality headset, and at least one patient location sensor to automatically scale and transform said medical images so as to create an overlay of least some of said medical images over any of a corresponding portion of said patient's anatomy and nearby said patient, for said user.

15. The system of claim 13, wherein said real-time biomedical sensor data comprises cardiovascular sensor data;
wherein said at least one computer processor is further configured to display said cardiovascular sensor data by animating a computer representation of said patient's heart and lungs to correspond with said cardiovascular sensor data, thereby producing a sensor responsive animation;
said at least one computer processor further configured to display said sensor responsive animation on said augmented reality headset.

16. The system of claim 15, wherein said at least one computer processor is further configured to modify said computer representation according to said medical history data, thus producing a medical history corrected computer representation;
said at least one computer processor further configured to display said sensor responsive animation on said augmented reality headset.

17. The system of claim 13, wherein said at least one computer processor is further configured to use any of said identity of said patient, said medical history data pertaining to said patient, and said real-time biomedical sensor data pertaining to said patient to retrieve from computer memory and display on said augmented reality headset, any of:
a) clinical decision algorithms;
b) alternative potential diagnoses;
c) alternative medical treatments.

18. The system of claim 13, wherein any of said augmented reality headset and said at least one computer processor in communication with said augmented reality headset are further configured to receive input from said user by any of voice sensors, hand motion sensors, facial gesture sensors, and haptic sensors.

19. The system of claim 13, wherein said augmented reality headset worn by a user comprises any of eyeglasses and goggles, with transparent lenses mounted over each eye allowing said user to see images of an outside world, at least one computer display configured to overlay said images of an outside world with computer generated bit-mapped graphics, at least one patient location sensor, at least one augmented reality headset computer processor configured to drive said bit-mapped graphics, and at least one communications interface configured to at least obtain medical history data from an outside source.

20. The system of claim 13, wherein said at least one computer processor is configured to obtain at least some of said real-time biomedical sensor data from a unitized patient wearable vital sign monitoring system configured to be capable of being worn by an ambulatory patient, said monitoring system comprising:
at least one ambulatory patient wearable sensor, said at least one ambulatory patient wearable sensor comprising any of one or more ECG sensors, pulse oximeters, electronic stethoscope sensors, temperature sensors, motion sensors, and blood pressure monitors;
said at least one ambulatory patient wearable sensor further configured to transmit sensor data either directly or indirectly to said augmented reality headset.

* * * * *